US012643850B2

(12) United States Patent
Schelwies et al.

(10) Patent No.: US 12,643,850 B2
(45) **Date of Patent: *Jun. 2, 2026**

(54) PREPARATION OF AROMATIC CARBOXYAMIDES BY PALLADIUM-CATALYZED CARBONYLATION REACTION

(71) Applicant: BASF SE, Ludwigshafen (DE)

(72) Inventors: Mathias Schelwies, Ludwigshafen (DE); Christopher Koradin, Ludwigshafen (DE); Rocco Paciello, Ludwigshafen (DE); Roland Goetz, Ludwigshafen (DE); Florian Vogt, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 760 days.

This patent is subject to a terminal disclaimer.

(21) Appl. No.: 17/921,206

(22) PCT Filed: Apr. 19, 2021

(86) PCT No.: PCT/EP2021/060084

§ 371 (c)(1),
(2) Date: Oct. 25, 2022

(87) PCT Pub. No.: WO2021/219418

PCT Pub. Date: Nov. 4, 2021

(65) Prior Publication Data

US 2023/0167050 A1 Jun. 1, 2023

(30) Foreign Application Priority Data

Apr. 29, 2020 (EP) .................................... 20172103

(51) Int. Cl.
*C07C 233/64* (2006.01)
*C07D 271/06* (2006.01)

(52) U.S. Cl.
CPC .......... *C07C 233/64* (2013.01); *C07D 271/06* (2013.01)

(58) Field of Classification Search
None
See application file for complete search history.

(56) References Cited

U.S. PATENT DOCUMENTS

| | | | |
|---|---|---|---|
| 3,988,358 A | 10/1976 | Heck | |
| 4,128,554 A | 12/1978 | Heck | |
| 5,344,961 A | 9/1994 | Drent | |
| 5,672,750 A | 9/1997 | Perry | |
| 6,271,372 B1 | 8/2001 | Roduit et al. | |
| 6,635,766 B1 | 10/2003 | Roduit et al. | |
| 2011/0172456 A1* | 7/2011 | Challand | C07C 67/36 562/459 |
| 2018/0251449 A1 | 9/2018 | Gaufreteau et al. | |
| 2019/0053492 A1 | 2/2019 | Wilcke et al. | |
| 2019/0276435 A1 | 9/2019 | Shepard et al. | |
| 2020/0002295 A1 | 1/2020 | Douty et al. | |

FOREIGN PATENT DOCUMENTS

| | | |
|---|---|---|
| WO | WO-2009/144197 A1 | 12/2009 |
| WO | WO-2015/185485 A1 | 12/2015 |
| WO | WO-2017/211649 A1 | 12/2017 |

OTHER PUBLICATIONS

Chen, et al., "Formates plus triazabicyclodecene (TBD): an efficient platform for non-gaseous carbonylation and unexpected hydrogenation", Organic Chemistry Frontiers, vol. 6, Issue 9, Mar. 8, 2019, pp. 1403-1408.
European Search Report for EP Patent Application No. 20172103.2 Issued on Sep. 17, 2020, 3 pages.
International Patent Application No. PCT/EP2021/060084, International Search Report and Written Opinion, Issued May 7, 2021.
Martinelli, et al., "Palladium-Catalyzed Aminocarbonylation of Aryl Chlorides at Atmospheric Pressure: The Dual Role of Sodium Phenoxide", Angewandte Chemie, vol. 46, Issue 44, Nov. 2, 2007, pp. 8460-8463.
Perry, et al., "Palladium-Catalyzed Carbonylation and Coupling Reactions of Aryl Chlorides and Amines", The Journal of Organic Chemistry, vol. 61, Issue 21, Oct. 18, 1996, pp. 7482-7485.
Schoenberg, et al., "Palladium-catalyzed carboalkoxylation of aryl, benzyl, and vinylic halides", The Journal of Organic Chemistry, vol. 39, Issue 23, Nov. 1, 1974, pp. 3318-3326.

* cited by examiner

*Primary Examiner* — Renee Claytor
*Assistant Examiner* — Jennifer C Sawyer
(74) *Attorney, Agent, or Firm* — MARSHALL, GERSTEIN & BORUN LLP

(57) ABSTRACT

Preparation of aromatic carboxyamides by palladium-catalyzed carbonylation reaction The present invention relates to a process for the preparation of aromatic carboxyamides of formula I, which can be obtained by palladium-catalyzed carbonylation reaction of aromatic chlorides of formula II, amines of formula III and carbon monoxide in the presence of a base. The invention further relates to a process for the preparation of aryl-5-trifluoromethyl-1,2,4-oxadiazoles, which are known for controlling phytopathogenic fungi.

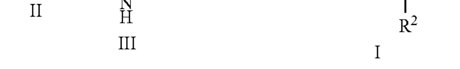

16 Claims, No Drawings

PREPARATION OF AROMATIC CARBOXYAMIDES BY PALLADIUM-CATALYZED CARBONYLATION REACTION

CROSS-REFERENCE TO RELATED APPLICATIONS

This is the U.S. national phase of International Application No. PCT/EP2021/060084, filed Apr. 19, 2021, which claims the benefit of European Patent Application No. 20172103.2, filed on Apr. 29, 2020.

The present invention relates to a process for the preparation of aromatic carboxyamides of formula I, which can be obtained by a palladium-catalyzed carbonylation reaction of aromatic chlorides of formula II, amines of formula III and carbon monoxide in the presence of a base. The invention further relates to a process for the preparation of aryl-5-trifluoromethyl-1,2,4-oxadiazoles, which have been described in the prior art for controlling phytopathogenic fungi, for example in WO 2015/185485 or in WO 2017/211649.

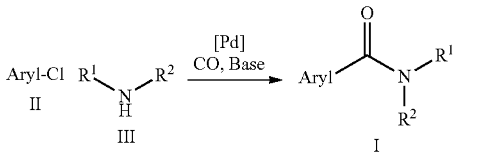

II III I

Carbonylation reactions for the preparation of aromatic carboxyamides of formula I are known in the prior art. These transformations are transition metal catalyzed processes that produce carboxyamides in one step from aryl halide, carbon monoxide and an amine. The procedure enables rapid access to versatile structural motives. In these reactions it is necessary to add a base to neutralize the hydrogen halide released in the reaction.

Heck et al. first reported palladium-catalyzed procedures of this type in *Journal of Organic Chemistry* 1974, 39, 3318 (and U.S. Pat. Nos. 3,988,358 and 4,128,554). Since then, many variations of this reaction type were described in the literature.

Economic interest predominantly focusses on the use of aromatic chlorides as they are both inexpensive and commercially well available. However, their relative chemically inertness makes them more challenging substrates in palladium-catalyzed carbonylation reactions, which is arguably the main reason why the majority of reported reactions make use of the more reactive aromatic bromides, iodides or trifluoromethylsulfonates. Batch reactions with aromatic chlorides typically require the presence of 2 mol % or more of the catalyst to allow for a complete conversion of the aromatic chloride. However, with such a high catalyst loading a transfer to industrial scale applications is in many cases prohibitive from an economic point of view. Also, high catalyst concentrations can lead to undesired catalyst precipitation under reaction conditions.

Perry et al. reported the increase of the conversion rate (at constant catalyst concentration) in an aminocarbonylation reaction of aromatic chlorides by adding halides, particularly sodium iodide (*Journal of Organic Chemistry* 1996, 61, 7482-7485 and in U.S. Pat. No. 5,672,750). The reaction of aromatic chlorides, carbon monoxide (5 psig or 0.34 bar (34 kPa)), 3 mol % palladium catalyst and 6 mol % of a bidentate phosphine ligand, 1.2 equivalents of 1,8-diazabicyclo-[5.4.0]undec-7-ene (DBU) and at least 1 equivalent of sodium iodide at 115° C. provided the carboxyamide in good yield in comparison with the same reaction without sodium iodide, which produced only minor amounts of the carboxyamide. The disadvantage of this process is that the use of halides generates additional costs, complicates work-up procedures and frequently leads to corrosion of the reactor.

Buchwald et al. (*Angew. Chem. Int. Ed.* 2007, 46, 8460-8463) describe the influence of the base in palladium-catalyzed aminocarbonylations of aromatic chlorides at atmospheric pressure. The procedures employ 2 mol % of a palladium catalyst, a bidentate phosphine ligand and 2 equivalents of the base at 120° C. The best yield was obtained with sodium phenoxide as the base. The use of DBU results in relatively low conversion of the aromatic chloride and poor yield of the carboxyamide.

WO 2009/144197 A1 discloses a method for producing aromatic and heteroaromatic carboxylic acids, carboxylic acid esters and carboxylic acid amides (carboxyamides). Reference is made to the preparation of carboxyamides starting from aniline and aromatic chlorides at 130-150° C. and 15 bar (1500 kPa) in the presence of a palladium catalyst and 1.5 equivalents of a base, for example DBU, triethylamine and potassium carbonate (working examples 6-1 to 6-3). The carboxyamides are obtained in low to moderate yields.

It was an object of the present invention to overcome the disadvantages of the known processes and to provide an improved and more economical and production plant friendly process, which enables the preparation of aromatic carboxyamides on an industrial scale, with an emphasis on low pressure reactions (less than 20 bar (2000 kPa)), wherein the catalyst is efficient enough to allow working at a low catalyst concentration (i.e. <0.5 mol % catalyst loading based on the amount aromatic chloride), and wherein the catalyst turnover rate is sufficiently stable so that full conversion can be achieved in a reasonable time. It is known, that improved catalyst stability translates into lower catalyst loading, which is required for an efficient conversion of the aromatic chloride.

The inventors surprisingly found that the process of the present invention provides a solution to these problems. The process of the present invention is cost efficient as it allows to use considerably lower amounts of the palladium catalyst than with previously reported procedures. The process of the invention is amenable to bases, that are affordable, and thus provide further advantages in an industrial setup. Moreover, the process of the invention does not require an exceedingly high carbon monoxide pressure.

Accordingly, the present invention relates to a process for preparing compounds of formula I,

I

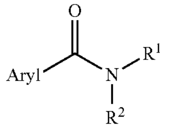

wherein

Aryl is phenyl or a 5- or 6-membered aromatic heterocycle; wherein the ring member atoms of the aromatic heterocycle include besides carbon atoms 1, 2, 3, or 4 heteroatoms selected from N, O, and S as ring member atoms with the provision that the heterocycle cannot contain 2 contiguous atoms selected from O and S; and wherein Aryl is further unsubstituted or further substituted with additional n identical or different radicals $R^A$; wherein n is 0,1, 2, 3, or 4;

$R^A$ is independently selected from the group consisting of fluorine, chlorine, cyano, $C_1$-$C_6$-alkyl, $C_1$-$C_6$-haloalkyl, $C_1$-$C_6$-alkoxy, $C_1$-$C_6$-haloalkoxy, —S(═O)$_2$—$CH_3$, —O—C≡N, —S—C≡N, —N═C═O, —N═C═S, di$C_1$-$C_6$-alkylamino, —C(═O)—$C_1$-$C_6$-alkyl, —C(═O)—O—$C_1$-$C_6$-alkyl, and —$CH_2$OH;

$R^1$ is $C_1$-$C_6$-alkyl, $C_1$-$C_6$-alkoxy, $C_3$-$C_8$-cycloalkyl, $C_3$-$C_8$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(═O)—$C_1$-$C_6$-alkyl, —C(═O)—O—$C_1$-$C_6$-alkyl, —C(═O)—N($C_1$-$C_6$-alkyl)$_2$, phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, —$NHSO_2$—$C_1$-$C_4$-alkyl, —(C═O)—$C_1$-$C_4$-alkyl, —C(═O)—O—$C_1$-$C_4$-alkyl, $C_1$-$C_6$-alkylsulfonyl, hydroxy$C_1$-$C_4$-alkyl, C(═O)—$NH_2$, C(═O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(═O)—$C_1$-$C_6$-alkyl, —C(═O)—$C_3$-$C_{11}$-cycloalkyl, or —C(═O)—O—$C_1$-$C_6$-alkyl; and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

the process comprising reacting an aromatic chloride of formula II,

Aryl-Cl II wherein Aryl is as defined above for compounds of formula I, with carbon monoxide and an amine compound of formula III,

III

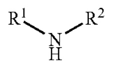

wherein $R^1$ and $R^2$ are as defined above for compounds of the formula I;

and wherein the reaction is carried out in the presence of a palladium-based catalyst, a solvent, and a base;

and wherein the process is characterized in that the base comprises a base b1 and a base b2, wherein b1 is at least one inorganic base selected from the group consisting of alkali metal and alkaline earth metal carbonates, hydrogen carbonates, acetates, alcoholates, hydroxides, and phosphates, or mixtures thereof;

b2 is a tertiary amine base or an imine base, which is present in an amount of less than 100 mol % based on the amount of the compound of formula II.

The carbonylation reaction of the present invention proceeds in the presence of a palladium-based catalyst selected from at least one Pd(II) compound or Pd(0) compound, or complexes which are obtained from Pd(II) compounds or Pd(0) compounds by complexing with ligands, particularly phosphine ligands. The palladium-based catalyst can be used either as a prefabricated complex or may be put together in situ combining the palladium compound and the ligands, or salts thereof.

Suitable palladium compounds or complexes are, for example, palladium(II)-acetate, palladium(II)-chloride, palladium(II)-bromide, palladium(II)-nitrate, palladium(II)-acetylacetonate, palladium(0)-dibenzylidenacetone-complex, palladium(0)-tetrakis(triphenylphosphine), palladium (0)-Bis(tri-o-tolylphosphine), palladium(0)(DPEphos) dicarbonyl, palladium(II)-propionate, palladium(II)-Bis (triphenylphosphine)dichloride, palladium(II)-(Bis (diphenylphosphino)ferrocene)dichloride, palladium(II)-nitrate, palladium(II)-Bis(acetonitrile)dichloride, palladium (II)-Bis(benzonitrile)dichloride, palladium(II)-hydroxide, palladium(0), [palladium(allyl)Cl]$_2$, palladium(0) on charcoal (Pd/C), and palladium(II)-bis(benzonitrile)-dichloride.

The carbonylation reaction preferably proceeds in the presence of a suitable Pd(II) compound or a Pd(0) compound that are complexed with ligands, especially monodentate or bidentate phosphine ligands.

Examples for preferred monodentate phosphines are trialkylphosphines, triarylphosphines, dialkylarylphosphines, alkyldiarylphoshines, cycloalkyldiarylphosphines, dicycloalkylarylphosphines, and tricycloalkylphosphines. Other examples for preferred phosphines are triheterocyclylphosphines und trihetarylphosphines. Examples for preferred trialkylphosphines are triethylphosphine, tri-n-butylphosphine, tri-tert-butylphosphine, tri-iso-propylphosphine, tribenzylphosphine. Examples for preferred tricycloalkylphosphines are tri(cyclopentyl)phosphine, tri(cyclohexyl)phosphine. Examples for preferred triarylphosphines are triphenylphosphine, tri(p-tolyl)phosphine, tri(m-tolyl)phosphine, tri(o-tolyl)phosphine, tri(p-methoxyphenyl)phosphine, tri(p-dimethylaminophenyl)phosphine, tri-(sodium-meta-sulfonatophenyl)-phosphine, diphenyl(2-sulfonatophenyl)phosphine, tri(1-naphthyl)phosphine and diphenyl-2-pyridylphosphine. Examples for preferred dialkylarylphosphines are dimethylphenylphosphine and di-tert-butylphenylphosphine.

Examples for preferred alkyldiarylphoshines are ethyldiphenylphosphine and isopropyldiphenylphosphine. An example for a preferred cycloalkyldiarylphosphine is cyclohexyldiphenylphosphine. An example for a preferred dicycloalkylarylphosphine is dicyclohexylphenylphosphine. Further examples for preferred triarylphosphines are tri(o-methoxyphenyl)phosphine, tri(m-methoxyphenyl)phosphine, tri(p-fluorphenyl)phosphine, tri(m-fluorphenyl)phosphine, tri(o-fluorphenyl)phosphine, tri(p-chlorphenyl) phosphine, tri(m-chlorphenyl)phosphine, tri (pentafluorphenyl)-phosphine, tris(p-trifluormethylphenyl) phosphine, tri[3,5-bis(trifluormethyl)phenyl]-phosphine, diphenyl(o-methoxyphenyl)phosphine, diphenyl(o-methylphenyl)phosphine, tris(3,5-dimethylphenyl)phosphine, and tri-2-naphthylphosphine. An example for a preferred trihetarylphoshine is tri(o-furyl)phosphine. An example for a preferred trialkylphosphine is triisobutylphosphine. An example for a preferred triheterocyclylphosphine is tris(1-pyrrolidinyl)phosphine. Particularly preferred are triphenylphosphine, di-tert-butylphenylphosphine, cyclohexyldiphenylphosphine, dicyclohexylphenylphosphine, tri(p-tolyl) phosphine and tri(cyclohexyl)phosphine.

Suitable bidentate phosphine ligands are 2,2'-Bis(diphenylphosphino)-1,1'-binaphthyl (BINAP), 2-Bis(diphenylphosphino)ethane (DPPE), 1,3-Bis(diphenylphosphino)-propane (DPPP), 1,4-Bis(diphenylphosphino)butane (DPPB), 1,1'-Bis(diphenylphosphino)ferrocene (DPPF), 4,5-Bis(diphenylphosphino)-9,9-dimethylxanthene (Xantphos), Bis(2-diphenylphosphino)phenyl]ether (DPEphos), 1,2-Bis(di-tert-butylphosphinomethyl)benzene, 1,2-Bis(di-tert-pentylphosphinomethyl)-benzene, 1,2-Bis(di-tert-butylphosphinomethyl)naphthaline, 2,2-dimethyl-1,3-Bis (diphenylphosphino)-propane, 1,3-Bis (diisoproylphosphino)-propane (DiPrPP), 1,3-Bis(tert-butylphosphino)-propane (DtBuPP), 1,3-Bis(n-butylphosphino)-propane (DnBuPP), 1,3-Bis (diisoproylphosphino)-ethan (DCPE), 1,3-Bis (dicyclohexylphosphino)-butane (DCPB), (1R)-1-[Bis(1,1-dimethylethyl)phosphino]-2-[(1R)-1-[bis(2-methylphenyl) phosphino]ethyl]ferrocene, (2R)-1-[(1R)-1-[Bis(1,1-dimethylethyl)phosphino]ethyl]-2-(dicyclohexylphosphino) ferrocene, (2R)-1-[(1R)-1-(dicyclohexylphosphino)ethyl]-2-(diphenylphosphino)ferrocene, (1R)-1-(dicyclohexylphosphino)-2-[(1R)-1-(dicyclohexylphosphino)ethyl]ferrocene, 2-ethyl-2-butyl-1,3-Bis(diphenylphosphino)-propane, and 1,3-Bis (dicyclohexylphosphino)-propane (DCPP). In a preferred embodiment the carbonylation reaction is carried out in the presence of a bidentate phosphine ligand; particularly DCPP.

Complexes with monodentate ligands of the type $L_2Pd(II)X_2$ or $Pd(0)L_4$ (X=anionic ligand; L=electroneutral phosphine ligand) are also suitable in the carbonylation reactions of the present invention, for example (tri(cyclohexyl)phosphine)$_2$Pd(II)$Cl_2$ or Pd(0)(triphenylphosphine)$_4$. Complexes with bidentate ligands of the type $LPd(II)X_2$, $Pd(0)L_2$ or $Pd(0)L_2(CO)_2$ are also suitable, for example (DCPP)Pd(II)$Cl_2$ or (DCPE)Pd(II)$Cl_2$. Many ligands are also available as salts, that can also be used in the present invention in combination with palladium compounds, for example P(tert-Bu)$_3$*$HBF_4$ or DCPP*2$HBF_4$.

In one aspect the carbonylation reaction is carried out in the presence of free phosphine, which means that the phosphine is used in excess so that part of it is not bound in the palladium-complex. The molar ratio of the phosphine ligand to palladium is typically between 0.5:1 to 10:1, preferably between 0.5:1 to 5:1.

The palladium-catalyst is used in an amount of less than 2 mol %, or less than 1 mol %, or less than 0.5 mol %, preferably between 0.001 to 0.3 mol %, more preferably between 0.001 to 0.2 mol %, based on the amount of the aromatic chloride of formula II.

Under the reaction conditions of the present invention the Pd-catalyst can undergo ligand exchange reactions so that the anionic ligands X and/or neutral Ligands L are replaced by other ligands, present in the reaction mixture, such as CO, amines or even parts of the substrate molecule (that can form complexes in significant amounts after elementary reactions such as oxidative addition or the arylhalide).

The palladium catalyst can be employed in homogenous solutions in the reaction medium or it may be formed from a heterogeneous catalyst precursor, for example colloidal Pd(0), Pd(0) applied to carrier materials, or Pd(II) compounds applied to carrier materials, for example Pd(0) or Pd(II) salts. Suitable carrier materials are for example inorganic metal oxides, silicates and carbon.

The palladium catalysts can be removed from the reaction mixture using conventional workup procedures that are known to the skilled person and, after isolation, can be used again in carbonylation reactions of the type described herein.

After a performed reaction the Pd-catalyst can be reused. To achieve this, chloride salts can be removed from the resulting reaction mixture by filtration, then the solvent can be removed by distillation, followed by product separation by filtration or distillation. The remaining residue contains most of the Palladium-catalyst, that can be reused for a subsequent amino carbonylation reaction. All operations have to be carried out in a way not influencing catalyst performance, i.e. handling under inert atmosphere can be necessary.

The carbonylation reaction of the present invention is conducted in the presence of carbon monoxide. This can mean that the reaction is carried out with pure carbon monoxide, or with mixtures of carbon monoxide with an inert gas, for example nitrogen or noble gases (helium, neon, argon). The carbonylation is typically carried out at atmospheric pressure or at elevated pressure in the reaction vessel. The term "elevated pressure" in the context of the present invention means a pressure above 1 bar (100 kPa). Suitable reaction vessels or reactors are known to the person skilled in the art, for example from "*Ullmanns Enzyklopädie der technischen Chemie*, Vol. 1, 3$^{rd}$ Edition, 1951, p. 769 ff.".

The partial pressure of carbon monoxide in a carbonylation according to the present invention is less than 100 bar (10000 kPa), preferably less than 50 bar (5000 kPa), more preferably less than 20 bar (2000 kPa), and, in a particularly preferred aspect, less than 15 bar (1500 kPa). In further aspects of the invention the partial pressure of carbon monoxide varies in the range between 0.1 and 200 bar (100 and 20000 kPa), between 1 and 100 bar (100 and 10000 kPa), between 1 and 50 bar (100 and 5000 kPa), between 2 and 20 bar (200 and 2000 kPa), or between 5 and 15 bar (500 and 1500 kPa).

In one embodiment the carbonylation reaction is carried out in the absence of, or with reduced amounts of oxygen or air.

The carbonylation, when carried out in a batchwise manner, requires batch times of from 1 hour to 100 hours, 2 hours to 50 hours, or 5 hours to 20 hours for a complete conversion of the aromatic chloride.

The temperature of the carbonylation reaction is suitably chosen in the range between 20° C. and 200° C.; preferably in the range between 50° C. and 180° C.; more preferably in the range between 50° C. and 150° C.; particularly in the range between 100° C. and 140° C.

The carbonylation can be carried out in the dark or upon irradiation of light (typical wavelength in the range 200 nm to 600 nm).

In one embodiment the carbonylation is carried out at a temperature in the range between 50 and 180° C. and at a partial pressure of carbon monoxide in the range between 1 and 100 bar (100 and 5.000 kPa).

In one embodiment the carbonylation reaction of the present invention is carried out at a temperature in the range between 50° C. and 150° C. and at a partial pressure of carbon monoxide in the range between 2 and 20 bar (200 and 2000 kPa).

In one embodiment the carbonylation reaction of the present invention is carried out at a temperature in the range between 100° C. and 140° C. and at a partial pressure of carbon monoxide in the range between 5 and 15 bar (500 and 1500 kPa).

The carbonylation reaction of the present invention is carried out in the presence of an inert solvent. Suitable solvents are, for example, aliphatic, cycloaliphatic and aromatic hydrocarbons (pentane, hexane, petroleum ether, cyclohexane, methylcyclohexane, benzene, toluene, xylene), aliphatic halogen-hydrocarbons (methylene chloride, chloroform, di- and tetrachloroethane), nitriles (acetonitrile, propionitrile, benzonitrile), ethers (diethylether, dibutylether, tert-butylmethylether, ethylene glycol dimethyl ether, ethylene glycol, diethyl ether, diethylene glycol dimethyl ether, 2-methyltetrahydrofuran, tetrahydrofuran, dioxane, diethylene, glycol monomethyl- or monoethyl ether), ketones (acetone, methyl isobutyl ketone), carboxylates and lactones (ethyl and methyl acetate, valerolactone), N-substituted lactams (N-methylpyrrolidone), carboxyamides (dimethylformamide, N,N-dimethylacetamide), acyclic ureas (dimethyl imidazolinum), nitriles as acetonitrile or propionitrile, and sulphoxides and sulphones (dimethyl sulphoxide, dimethyl sulphone, tetramethylene sulphoxide, tetramethylene sulphone). Preferred solvents that are typically polar organic solvents such as tetrahydrofuran, dimethylformamide, N-methylpyrrolidone, dioxane, 2-methyltetrahydrofuran, N,N-dimethylacetamide, toluene, acetonitrile.

The carbonylation reaction of the present invention is carried out in the presence of an inorganic base b1 to neutralize the hydrogen chloride furnished in the course of the reaction. Examples for preferred inorganic bases b1 are alkali metal and alkaline earth metal carbonates (for example $Na_2CO_3$, $K_2CO_3$, or $MgCO_3$), hydrogen carbonates (for example $NaHCO_3$, $KHCO_3$, or $Mg(HCO_3)_2$), hydroxides, acetates, alcoholates, phosphates and hydrogen phosphates, which provide the advantage that they are not expensive, convenient to handle and an aqueous workup allows for their easy removal after the carbonylation reaction is finished. Preferred alkali metal carbonates are sodium and potassium carbonate, particularly potassium carbonate. Preferred alkaline earth metal carbonates are magnesium and calcium carbonates. Preferred alkali metal phosphates are sodium phosphate ($Na_3PO_4$), potassium phosphate ($K_3PO_4$) and disodium hydrogen phosphate ($Na_2HPO_4$).

In a preferred embodiment the base b1 is an alkali metal carbonate, alkali metal phosphate, alkali metal hydrogen phosphate, alkali metal hydroxide, or an alkali metal acetate.

In a more preferred embodiment the base b1 is an alkali metal carbonate or an alkali metal acetate. In a particularly preferred embodiment the base b1 is sodium carbonate or sodium acetate.

Base b1 is used in an amount of at least 80 mol %, or at least 100 mol %, or at least 150 mol %, based on the amount of the compound of formula II. In another aspect of the present invention the base b1 is used in an amount that ranges between 80 and 1.000 mol % based on the amount of the compound of formula II. In a further aspect of the present invention the base b1 is used in an amount that ranges between 80 and 500 mol % based on the amount of the compound of formula II. In yet another aspect the base b1 is used in an amount that ranges between 90 and 150 mol % based on the amount of the compound of formula II.

In a preferred embodiment of the present invention the carbonylation reaction employs sodium carbonate or potassium carbonate as base b1 in an amount that ranges between 90 and 150 mol % based on the amount of the compound of formula II; particularly base b1 is potassium carbonate; and TBD or DBU as base b2, in an amount that ranges between 1 and 10 mol %, based on the amount of the compound of formula II.

The carbonylation reactions of the present invention employ a tertiary amine base or an imine base b2 in addition to base b1.

The term "tertiary amine base" in the context of the present invention means an amine compound containing at least one nitrogen atom that is substituted with 3 alkyl substituents.

The term "imine base" in the context of the present invention means an amine compounds which contains at least one imine group "—N═".

In one embodiment base b2 is a tertiary amine base or an imine base selected from the group consisting of 1,4-diazabicyclo[2.2.2]octan (DABCO), N-methylpiperidine, lutidine, pyridine, and a base of the formula B.2,

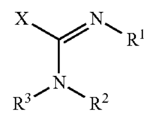

B.2 wherein

X is $NR^4R^5$ or $C_1$-$C_4$-alkyl;

$R^1$, $R^2$, $R^3$, $R^4$, $R^5$ independently of each other are hydrogen or $C_1$-$C_4$-alkyl; or $R^1$ and $R^2$ together with the interjacent atoms between these radicals form a 5-, 6- or 7-membered ring, which contains besides carbon atoms 2 nitrogen atoms;

or, if X is $NR^4R^5$, $R^3$ and $R^4$ together with the interjacent atoms between these radicals form a 5-, 6- or 7-membered ring, which contains besides carbon atoms 1 or 2 nitrogen atoms;

or, if X is $C_1$-$C_4$-alkyl, $R^3$ and X together with the interjacent atoms between these radicals form a 5-, 6- or 7-membered ring, which contains besides carbon atoms 1 or 2 nitrogen atoms.

In another embodiment base b2 is an amine selected from the group consisting of 1,4-diazabicyclo[2.2.2]octan (DABCO), N-methylpiperidine, lutidine, pyridine, and a base of the formula B.2, wherein X is $NR^4R^5$ or $C_1$-$C_4$-alkyl;

$R^1$, $R^2$, $R^3$, $R^4$, $R^5$ independently of each other are hydrogen or $C_1$-$C_4$-alkyl;

or $R^1$ and $R^2$ together with the interjacent atoms between these radicals form a 5-, 6- or 7-membered ring, which contains besides carbon atoms 2 nitrogen atoms;

and, if X is $NR^3R^4$, $R^3$ and $R^4$ together with the interjacent atoms between these radicals form a 5-, 6- or 7-membered ring, which contains beside carbon atoms 1 or 2 nitrogen atoms;

and, if X is $C_1$-$C_4$-alkyl, $R^3$ and X together with the interjacent atoms between these radicals form a 5-, 6- or 7-membered ring, which contains besides carbon atoms 1 or 2 nitrogen atoms.

In a further embodiment base b2 is an amine selected from the group consisting of 1,4-diazabicyclo[2.2.2]octan (DABCO), 1,5-diazabicyclo[4.3.0]non-5-ene (DBN), 1,5,7-triazabicyclo[4.4.0]dec-5-ene (TBD), and 1,8-diazabicyclo [5.4.0]undec-7-ene (DBU), N-methylpiperidine, lutidine, pyridine.

In a preferred embodiment base b2 is DBN, TBD, or DBU. In a more preferred embodiment base b2 is TBD or DBU; particularly base b2 is DBU.

In one aspect of the present invention the base b2 is present in an amount of less than 100 mol % based on the amount of the compound of formula II, preferably less than 50 mol %, more preferably less than 10 mol %, particularly less than 5 mol %. In another aspect the base b2 is used in an amount that ranges between 0.1 and 50 mol % based on the amount of the compound of formula II. In a further aspect the base b2 is used in an amount that ranges between 1 and 20 mol % based on the amount of the compound of formula II. In another aspect the base b2 is used in an amount that ranges between 1 and 10 mol % based on the amount of the compound of formula II. In one embodiment the base b2 is used in an amount that ranges between 1 and 5 mol % based on the amount of the compound of formula II.

The molar ratio of compound of formula III to compound of formula II is typically between 0.8:1 to 10:1, preferably between 1:1 to 5:1, more preferably between 1:1 to 2:1.

In one embodiment of the invention the aromatic chloride used in the carbonylation process is of formula II.a, II.a

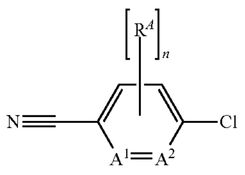

wherein n is 0 or 1; $A^1$ and $A^2$ are independently selected from nitrogen, C—H, or C—$R^A$; and wherein no more than one of $A^1$ and $A^2$ is nitrogen; and wherein $R^A$ is as defined or preferably defined herein for compounds of formula I, to obtain an aromatic carboxyamide of formula La, I.a

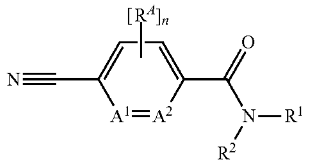

wherein the variables n, $R^A$, $A^1$, and $A^2$ have the meaning as defined for compounds II.a and wherein the variables $R^1$ and $R^2$ have the meaning as defined for compounds of formula I.

In one embodiment of the invention the aromatic chloride used in the carbonylation process is of formula II.b, II.b

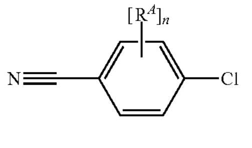

wherein n is 0 or 1 and $R^A$ is as defined or preferably defined herein for compounds of formula I, to obtain an aromatic carboxamide of formula I.b, I.b

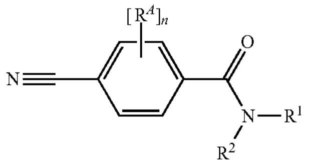

wherein the variables n and $R^A$ have the meaning as defined for compounds II.b and wherein the variables $R^1$ and $R^2$ have the meaning as defined or preferably defined herein for compounds of formula I.

Compounds of formula II.a and II.b are either commercially available or may be prepared using standard procedures known to a person skilled in the art from readily available starting materials.

In one aspect of the present invention the variable A is phenyl in compounds of formula I.

In one embodiment of the present invention radical $R^A$ in compounds of formula I, I.a, I.b, II, II.a, and II.b is fluorine, chlorine, CN, methyl, ethyl, n-propyl, iso-propyl, $CF_3$, $CHF_2$, $CH_2F$, —S(═O)$_2$—$CH_3$, —C(═O)—O-ethyl, —C(═O)—O-methyl, —C(═O)-ethyl, —C(═O)-methyl.

In one embodiment of the present invention radical $R^A$ in compounds of formula I, I.a, I.b, II, II.a, and II.b is fluorine, chlorine, CN, methyl, ethyl, $CF_3$, —S(═O)$_2$—$CH_3$, —C(═O)—O-ethyl, —C(═O)—O-methyl, —C(═O)-ethyl, —C(═O)-methyl.

In one aspect the variable n is 1 and $R^A$ is fluorine in compounds of formula I, I.a, I.b, II, II.a, and II.b.

In a preferred embodiment the variable n is 0 in compounds of formula I, I.a, I.b, II, II.a, and II.b.

Further embodiments relate to the meaning of the variables $R^1$ and $R^2$ in compounds of formulae I, III, I.a and I.b, IV, V, and VI.

One embodiment relates to the preparation of compounds of formulae I, III, I.a and I.b, IV, V, and VI, wherein $R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy, and cyclopropyl; and $R^2$ is hydrogen, methyl, or ethyl.

Another embodiment relates to the preparation of compounds of formulae I, III, I.a and I.b, IV, V, and VI, wherein $R^1$ is methyl or phenyl, wherein the phenyl ring is unsubstituted or substituted with 1, 2, 3, or 4 identical or different groups selected from halogen; and wherein $R^2$ is hydrogen, methyl, or ethyl.

A further embodiment relates to the preparation of compounds of formulae I, III, I.a and I.b, IV, V, and VI, wherein $R^1$ is methyl, 2-methoxyiminoethyl, bicyclo[1.1.1]pentan-1-yl, 2-fluoro-phenyl, 4-fluoro-phenyl, or 2-difluoromethoxy-phenyl; and $R^2$ is hydrogen.

Yet another embodiment relates to the preparation of compounds of formulae I, III, I.a and I.b, IV, V, and VI, wherein $R^1$ is methyl, 2-fluoro-phenyl, 4-fluoro-phenyl, or 2,4-difluoro-phenyl; in particular methyl or 2-fluoro-phenyl; and wherein $R^2$ is hydrogen.

In a preferred embodiment (embodiment E.1) of the present invention the carbonylation reaction employs sodium carbonate or potassium carbonate as base b1 in an amount that ranges between 90 and 150 mol %, based on the amount of the compound of formula II; in particular base b1 is potassium carbonate; and TBD or DBU as base b2, in an amount that ranges between 1 and 30 mol %, based on the amount of the compound of formula II.

Embodiment E.2: is based on embodiment E.1, wherein the carbonylation is carried out at a temperature in the range between 90° C. and 140° C. and at a partial pressure of carbon monoxide in the range between 5 and 15 bar (500 and 1500 kPa).

Embodiment E.3: is based on embodiment E.2, whereas the reaction is carried out in the presence of a palladium-catalyst in an amount of less than 2 mol %, based on the amount of the compound of formula II; and wherein at least one organic mono- or bidentate phosphine ligand is used for the palladium-catalyst selected from the group consisting of triphenylphosphine, tri(tolyl)phosphine, tri-n-butylphosphine, tricyclohexylphosphine, tri-iso-propylphosphine, tri-tert-butylphosphine, S-phos (2-dicyclohexylphosphino-2',6'-dimethoxybiphenyl), cyclohexyldiphenylphosphine, triisopropylphosphine, phenyldicycloheylphosphine, butyldiadamantylphosphine, 1,2-Bis(dimethylphosphino)ethane, 2,2'-Bis(diphenylphosphino)-1,1'-binaphthyl (BINAP), 2-Bis(diphenylphosphino)ethane (DPPE), 1,3-Bis(diphenylphosphino)-propane (DPPP), 1,4-Bis(diphenylphosphino)butane (DPPB), 1,1'-Bis(diphenylphosphino)ferrocene (DPPF), 4,5-Bis(diphenylphosphino)-9,9-dimethylxanthene (Xantphos), Bis(2-diphenylphosphino)phenyl]ether (DPEphos), 1,2-Bis(di-tert-butylphosphinomethyl)benzene, 1,2-Bis(di-tert-pentylphosphinomethyl)-benzene, 1,2-Bis(di-tert-butylphosphinomethyl)naphthaline, 2,2-dimethyl-1,3-Bis(diphenylphosphino)-propane, 1,3-Bis(diisoproylphosphino)-propane (DiPrPP), 1,3-Bis(tert-butylphosphino)-propane (DtBuPP), 1,3-Bis(n-butylphosphino)-propane (DnBuPP), 1,3-Bis(diisoproylphosphino)-ethan (DCPE), 1,3-Bis(dicyclohexylphosphino)-butane (DCPB), (1R)-1-[Bis(1,1-dimethylethyl)phosphino]-2-[(1R)-1-[Bis(2-methylphenyl)phosphino]ethyl]ferrocene, (2R)-1-[(1R)-1-[Bis(1,1-dimethylethyl)phosphino]ethyl]-2-(dicyclohexylphosphino)ferrocene, (2R)-1-[(1R)-1-(dicyclohexylphosphino)ethyl]-2-(diphenylphosphino)ferrocene, (1R)-1-(dicyclohexylphosphino)-2-[(1R)-1-(dicyclohexylphosphino)ethyl]ferrocene, 2-ethyl-2-butyl-1,3-Bis(diphenylphosphino)-propane, and 1,3-Bis(dicyclohexylphosphino)-propane (DCPP); and wherein the molar ratio of the phosphine ligand to palladium is between 0.5:1 to 5:1.

Embodiment E.4: is based on embodiment E.3, wherein the molar ratio of compound of formula III to compound of formula II is between 1:1 to 2:1.

Embodiment E.5: is based on embodiment E.4, wherein the solvent is tetrahydrofuran, dimethylformamide, N-methylpyrrolidone, dioxane, 2-methyltetrahydrofuran, N,N-dimethylacetamide, toluene, or acetonitrile.

Embodiment E.6: is based on embodiment E.5, wherein the process relates to the preparation of compounds of formulae Ib, IV, V, and VI, wherein $R^1$ is methyl or 2-fluoro-phenyl; and wherein $R^2$ is hydrogen.

Compounds of formula I.b can be further transformed to obtain compounds of formula IV, wherein the variables $R^A$, n, $R^1$ and $R^2$ are as defined or preferably defined herein. Compounds IV are valuable chemical intermediates for the synthesis of 3-aryl-5-trifluoromethyl-1,2,4-oxadiazoles, which are known to be useful for controlling phytopathogenic fungi.

IV

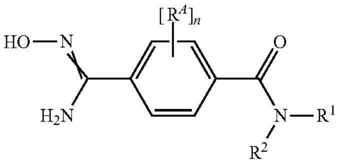

Accordingly, compounds of formula IV can be obtained by treatment of compounds of formula I.b with hydroxylamine or a salt thereof, for example the hydrochloride salt, in the presence of a base, preferably triethylamine, sodium hydroxide or sodium methylate, in a suitable solvent, such as methanol, ethanol or water, or a mixture of these solvents, at a temperature between 0° C. and 100° C. For related examples see Kitamura, S. et al Chem. Pharm. Bull. 2001, 49, 268 or any one of the patent references cited above.

Typically, the preparation of fungicidal 3-aryl-5-trifluoromethyl-1,2,4-oxadiazoles involves the formation of the oxadiazole ring through the reaction of hydroxyamidine compounds of formula IV with an activated derivative of trifluoroacetic acid. Accordingly, in a further embodiment of the present invention, the compound of formula IV is reacted with an activated species of trifluoroacetic acid to obtain a compound of formula V, wherein the variables $R^A$, n, $R^1$ and $R^2$ are as defined or preferably defined herein.

V

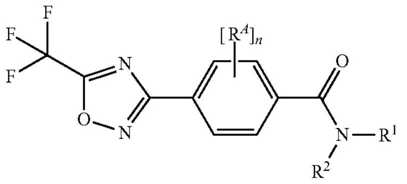

Procedures for the oxadiazole formation are described in WO 2017/198852, WO 2017/207757, WO 2017220485, WO 2018/065414, WO 2019/020451, and in WO 2017/211652 A1.

Another embodiment of the present invention relates to the process further comprising the step of reacting the compound of formula V to obtain a compound of formula VI, wherein the variables $R^A$, n, $R^1$ and Ware as defined or preferably defined herein.

VI

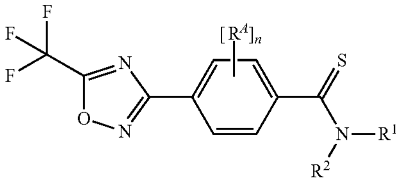

Compounds of formula VI can be prepared from compounds of formula V by treatment with Lawesson's reagent or phosphorus pentasulfide in an inert organic solvent, such as non-halogenated aliphatic hydrocarbons, non-halogenated cycloaliphatic hydrocarbons, halogenated aliphatic hydrocarbons, halogenated aromatic hydrocarbons, amides, ethers, esters, ketones, nitriles; for example toluene, tetrahydrofuran, dioxane or ethyl acetate; at a temperature between 0° C. and 130° C., preferentially between 60° C. and 80° C. For examples, see *Eur. J. Med. Chem.* 2011, 46(9), 3917-3925; Synthesis 2003, 13, 1929-1958, WO 2006/0123242, WO 2010/086820, WO 2014/0151863, WO 2019/020451 and WO 2017/211649. After completion of the reaction the reaction mixture is worked up in the usual manner.

In particular, the present invention relates to the preparation of compounds V.a, V.b and VI.a.

V.a

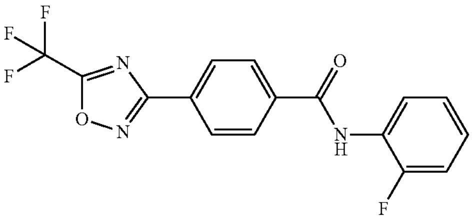

V.b

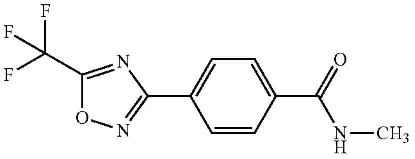

VI.a

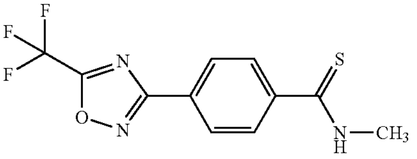

In the definitions of the variables given above, collective terms are used which are generally representative for the substituents in question.

The term "$C_n$-$C_m$" indicates the number of carbon atoms possible in each case in the substituent or substituent moiety in question.

The term "halogen" refers to fluorine, chlorine, bromine and iodine.

The term "oxo" refers to an oxygen atom =O, which is bound to a carbon atom or sulfur atom, thus forming, for example, a ketonyl —C(=O)— or sulfinyl —S(=O)— group.

The term "formyl" refers to a group C(=O)H.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or hetereoaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_4$-alkoxyimino" refers to a divalent imino radical ($C_1$-$C_4$-alkyl-O—N═) carrying one $C_1$-$C_4$-alkoxy group as substituent, e.g. methylimino, ethylimino, propylimino, 1-methylethyl-imino, butylimino, 1-methylpropylimino, 2-methylpropylimino, 1,1-dimethylethylimino and the like.

The term "$C_1$-$C_6$-alkoxyimino-$C_1$-$C_4$-alkyl" refers to alkyl having 1 to 4 carbon atoms, wherein two hydrogen atoms of one carbon atom of the alkyl radical are replaced by a divalent $C_1$-$C_6$-alkoxyimino radical ($C_1$-$C_6$-alkyl-O—N═) as defined above.

The term "$C_2$-$C_6$-alkenyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkenyloxyimino radical ($C_2$-$C_6$-alkenyl-O—N═).

The term "$C_2$-$C_6$-alkynyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkynyloxyimino radical ($C_2$-$C_6$-alkynyl-O—N═).

The term "hydroxy$C_1$-$C_4$-alkyl" refers to alkyl having 1 to 4 carbon atoms, wherein one hydrogen atom of the alkyl radical is replaced by a OH group.

The term "amino$C_1$-$C_4$-alkyl" refers to alkyl having 1 to 4 carbon atoms, wherein one hydrogen atom of the alkyl radical is replaced by a $NH_2$ group.

The term "$C_1$-$C_6$-alkylamino" refers to an amino group, which is substituted with one residue independently selected from the group that is defined by the term $C_1$-$C_6$-alkyl. Likewise, the term "di$C_1$-$C_6$-alkylamino" refers to an amino group, which is substituted with two residues independently selected from the group that is defined by the term $C_1$-$C_6$-alkyl.

The term "$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $C_1$-$C_4$-alkyl-NH— group which is bound through the nitrogen. Likewise, the term "di$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a ($C_1$-$C_4$-alkyl)$_2$N— group which is bound through the nitrogen.

The term "aminocarbonyl-$C_1$-$C_4$-alkyl" refers to alkyl having 1 to 4 carbon atoms, wherein one hydrogen atom of the alkyl radical is replaced by a —(C═O)—$NH_2$ group.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_3$-$C_{11}$-cycloalkyl" refers to a monocyclic, bicyclic or tricyclic saturated univalent hydrocarbon radical having 3 to 11 carbon ring members that is connected through one of the ring carbon atoms by substitution of one hydrogen atom, such as cyclopropyl ($C_3H_5$), cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.1.1]hexyl, norcaranyl (bicyclo[4.1.0]heptyl) and norbornyl (bicyclo[2.2.1]heptyl). Further examples of bicyclic or tricyclic cycloalkyl radicals are found herein as examples $R^1$.1 to $R^1$.57.

The term "$C_3$-$C_{11}$-cycloalkyl" refers to a monocyclic, bicyclic or tricyclic saturated univalent hydrocarbon radical having 3 to 11 carbon ring members that is connected through one of the ring carbon atoms by substitution of one hydrogen atom, such as cyclopropyl ($C_3H_5$), cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.1.1]hexyl, norcaranyl (bicyclo[4.1.0]heptyl) and norbornyl (bicyclo[2.2.1]heptyl).

The term "$C_3$-$C_{11}$-cycloalkyl-$C_1$-$C_6$-alkyl" refers to alkyl having 1 to 11 carbon atoms, wherein one hydrogen atom of the alkyl radical is replaced by a $C_3$-$C_{11}$-cycloalkyl group as defined above.

The term "$C_3$-$C_{11}$-cycloalkoxy" refers to a cyclic univalent hydrocarbon radical having 3 to 11 carbon ring members (as defined above) that is bonded via an oxygen, at any position in the cycloalkyl group, for example cyclopropyloxy.

The terms "—C(═O)—$C_1$-$C_4$-alkyl", "—C(═O)—O—$C_1$-$C_4$-alkyl" and "—C(═O)—$C_3$-$C_{11}$-cycloalkyl" refer to radicals which are attached through the carbon atom of the —C(═O)— group.

The term "aliphatic" refers to compounds or radicals composed of carbon and hydrogen and which are non-aromatic compounds. An "alicyclic" compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted with . . . " refers to aliphatic groups, cyclic groups and groups, which contain an aliphatic and a cyclic moiety in one group, such as in, for example, $C_3$-$C_3$-cycloalkyl-$C_1$-$C_4$-alkyl; therefore a group which contains an aliphatic and a cyclic moiety both of these moieties may be substituted or unsubstituted independently of each other.

The term "phenyl" refers to an aromatic ring systems including six carbon atoms (commonly referred to as benzene ring.

The term "heteroaryl" refers to aromatic monocyclic or polycyclic ring systems including besides carbon atoms, 1, 2, 3 or 4 heteroatoms independently selected from the group consisting of N, O and S.

The term "saturated 3- to 7-membered carbocycle" is to be understood as meaning monocyclic saturated carbocycles having 3, 4 or 5 carbon ring members. Examples include cyclopropyl, cyclopentyl, cyclohexyl, cycloheptyl, and the like.

The term "3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms", is to be understood as meaning both, aromatic mono- and bicyclic heteroaromatic ring systems, and also saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine;

and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, hexahydroazepin-1-, -2-, -3- or -4-yl, tetra- and hexahydrooxepinyl such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, hexahydroazepin-1-, -2-, -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

WORKING EXAMPLES

The present invention is further illustrated by means of the following working examples.

Example 1) Preparation of 4-cyano-N-(2-fluorophenyl)-benzamide (Example not According to the Invention)

Palladium(II)chloride (3.8 mg, 0.021 mmol), 1,3-Bis(dicyclohexylphosphino)propane bis(tetrafluoroborate) (DCPP*$HBF_4$, 12.9 mg, 0.021 mmol), potassium carbonate (1.12 g, 8.1 mmol) and 4-chlorobenzonitrile (1.12 g, 8.1 mmol) were kept under argon in an autoclave. 2-Fluoroaniline (1.74 g, 15.7 mmol) and tetrahydrofuran (10 mL) were added under argon and carbon monoxide was introduced into the reaction vessel at a pressure of 10 bar (1000 kPa). The reaction mixture was stirred at 130° C. for 20 hours (stirring rate 1000 rpm). Then, the reaction mixture was cooled to room temperature followed by the release of the pressure. GC-conversion*: 45%; selectivity regarding carboxyamide: 95%.

Except otherwise noted each of the Examples 2, 3, 1.1 to 1.6 of Table 1 below reproduced the same reaction conditions as Example 1 above. Examples 1.1 to 1.6 represent variations according to the present invention, as they included catalytic amounts of DBU, based on the amount of 4-chlorobenzonitrile, in addition to stoichiometric amounts of a base of type b1.

It was observed that, at low catalyst concentration, the reaction eventually stopped and did not achieve desirable degrees of conversions (Example 1, the catalyst composition leads to conversions of 45% after 20 hours reaction time). If the reaction time was prolonged to 40 hours, 72% conversion was observed under these conditions (Example 2). Example 3 illustrates that equimolar amounts of DBU based on the amount of 4-chlorobenzonitrile, and in the absence of a base of type b1, did not lead to an increase in conversion after 20 hours.

It was surprisingly found that upon addition of catalytic amounts of a base b2 (DBU, 5 mol %) significantly higher conversions were achieved (Examples 1.1 and 1.2). Example 1.2 shows that a prolongation of the reaction time to 40 hours leads to 88% conversion as compared to 72% conversion in Example 2. Examples 1.3 to 1.5 illustrate that different Pd and ligand sources were successfully used. Example 1.6 shows that potassium carbonate (base b1) could be exchanged with another base.

Aryl is phenyl or a 5- or 6-membered aromatic heterocycle; wherein the ring member atoms of the aromatic heterocycle include besides carbon atoms 1, 2, 3, or 4 heteroatoms selected from N, O, and S as ring member atoms with the provision that the heterocycle cannot contain 2 contiguous atoms selected from O and S; and wherein Aryl is further unsubstituted or further substituted with additional n identical or different radicals $R^A$; wherein n is 0, 1, 2, 3, or 4;

$R^A$ is independently selected from the group consisting of fluorine, chlorine, cyano, $C_1$-$C_6$-alkyl, $C_1$-$C_6$-haloalkyl, $C_1$-$C_6$-alkoxy, $C_1$-$C_6$-haloalkoxy, —S(═O)$_2$—$CH_3$, —O—C≡N, —S—C≡N, —N═C═O, —N═C═S, di$C_1$-$C_6$-alkylamino, —C(═O)—$C_1$-$C_6$-alkyl, —C(═O)—O—$C_1$-$C_6$-alkyl, and —$CH_2OH$;

$R^1$ is $C_1$-$C_6$-alkyl, $C_1$-$C_6$-alkoxy, $C_3$-$C_{11}$-cycloalkyl, $C_3$-$C_5$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino,

TABLE 1

| Example | Pd (mol %) | Ligand (mol %) | DBU (mol %) | Reaction time (hours) | Conversion after reaction time | Selectivity amide (GC*) |
|---|---|---|---|---|---|---|
| 1 [a), b)] | $PdCl_2$ (0.25) | DCPP*$HBF_4$ (0.25) | — | 20 | 45% | 95% |
| 2 [b)] | $PdCl_2$ (0.25) | DCPP*$HBF_4$ (0.25) | — | 40 | 72% | 95% |
| 3 [b), e)] | $PdCl_2$ (0.25) | DCPP*$HBF_4$ (0.25) | 100 | 20 | 42% | 99% |
| 1.1 [c)] | $PdCl_2$ (0.25) | DCPP*$HBF_4$ (0.25) | 5 | 20 | 76% | 98% |
| 1.2 [c)] | $PdCl_2$ (0.25) | DCPP*$HBF_4$ (0.25) | 5 | 40 | 88% | 96% |
| 1.3 [c)] | Pd/C [d)] (0.25) | DCPP*$HBF_4$ (0.25) | 5 | 20 | 89% | 98% |
| 1.4 [c)] | $Pd(OH)_2$ 0.25) | DCPP*$HBF_4$ (0.25) | 5 | 20 | 82% | 98% |
| 1.5 [c)] | $PdCl_2$ DCPP (0.25) | — | 5 | 20 | 71% | 96% |
| 1.6 [c), f)] | $PdCl_2$ (0.25) | DCPP*$HBF_4$ (0.25) | 5 | 20 | 76% | 97% |

[a)] identical with Example 1) above;
[b)] example not according to the invention;
[c)] example representing the present invention;
[d)] Pd(10%) on charcoal, mol % relates to the molar amount of Pd;
[e)] no potassium carbonate present;
[f)] sodium carbonate was used instead of potassium carbonate

*Analytical GC method: VF-23 column (60 m x 0.25 mm/0.25 μm; temperature: 2 min at 50° C. then 10° C./min up to 100° C.; then 15° C./min up to 200° C.; 5 min at 200° C.; then 20° C./min up to 250° C.; flow: 2.0 mL/min; hydrogen as carrier gas). $t_R$ (2-fluoroaniline) = 10.9 min; $t_R$ (4-chlorobenzonitrile) = 12.5 min; $t_R$ (carboxyamide) = 34.3 min.

The invention claimed is:

1. A process for preparing an aromatic carboxyamide of formula I,

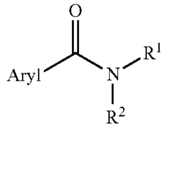

I wherein

—C(═O)—$C_1$-$C_6$-alkyl, —C(═O)—O—$C_1$-$C_6$-alkyl, —C(═O)—N($C_1$-$C_6$-alkyl) 2, phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, —$NHSO_2$—$C_1$-$C_4$-alkyl, —(C═O)—$C_1$-$C_4$-alkyl, —C(═O)—O—$C_1$-$C_4$-alkyl, $C_1$-$C_6$-alkylsulfonyl, hydroxy$C_1$-$C_4$-alkyl, C(═O)—$NH_2$, C(═O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(═O) H, —C(═O)—$C_1$-$C_6$-alkyl, —C(═O)—$C_3$-$C_{11}$-cycloalkyl, or —C(═O)—O—$C_1$-$C_6$-alkyl; and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

the process comprising reacting an aromatic chloride of formula II,

Aryl-Cl II wherein Aryl is as defined above for compounds of formula I, with carbon monoxide and an amine compound of formula III,

III

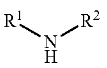

wherein $R^1$ and $R^2$ are as defined above for compounds of the formula l;

and wherein the reaction is carried out in the presence of a palladium-based catalyst, a solvent, and a base;

and wherein the process is characterized in that the base comprises a base b1 and a base b2, wherein b1 is at least one inorganic base selected from the group consisting of alkali metal and alkaline earth metal carbonates, hydrogen carbonates, acetates, alcoholates, hydroxides, and phosphates, or mixtures thereof;

b2 is a tertiary amine base or an imine base, which is present in an amount of less than 100 mol % based on the amount of the compound of formula II.

2. The process according to claim 1, wherein Aryl is phenyl.

3. The process according to claim 1, wherein the aromatic chloride is of formula II.b, II.b

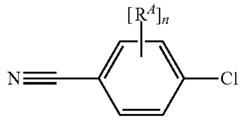

wherein n is 0 or 1 and $R^A$ is as defined above for compounds of formula I to obtain an aromatic carboxyamide of formula I.b I.b

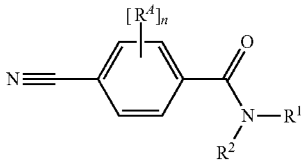

wherein the variables n and $R^A$ have the meaning as defined for compounds II.b and wherein the variables $R^1$ and $R^2$ have the meaning as defined above for compounds of formula I.

4. The process according to claim 1, wherein n is 0.

5. The process according to claim 1, wherein in compounds of formulae I and III $R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, methyl, ethyl, methoxy, trifluoromethyl, trifluoromethoxy, difluoromethyl, difluoromethoxy, and cyclopropyl; and $R^2$ is hydrogen, methyl, or ethyl.

6. The process according to claim 1, wherein in compounds of formulae I and III $R^1$ is methyl or phenyl, wherein the phenyl ring is unsubstituted or substituted with 1, 2, 3, or 4 identical or different groups selected from halogen; and wherein $R^2$ is hydrogen, methyl, or ethyl.

7. The process according to claim 1, wherein in compounds of formulae I and III $R^1$ is methyl or 2-fluoro-phenyl; and wherein $R^2$ is hydrogen.

8. The process according to claim 1, wherein the base b1 is an alkali metal carbonate or an alkali metal acetate.

9. The process according to claim 1, wherein the base b1 is used in an amount that ranges between 90 and 150 mol %, based on the aromatic chloride of formula II.

10. The process according claim 1, wherein the base b2 is an amine selected from the group consisting of DABCO, N-methylpiperidine, lutidine, pyridine, and a base of the formula B.2,

B.2

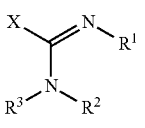

wherein

X is $NR^4R^5$ or $C_1$-$C_4$-alkyl;

$R^1$, $R^2$, $R^3$, $R^4$, $R^5$ independently of each other are hydrogen or $C_1$-$C_4$-alkyl; or $R^1$ and $R^2$ together with the interjacent atoms between these radicals form a 5-, 6- or 7-membered ring, which contains besides carbon atoms 2 nitrogen atoms;

or, if X is $NR^4R^5$, $R^3$ and $R^4$ together with the interjacent atoms between these radicals form a 5-, 6- or 7-membered ring, which contains besides carbon atoms 1 or 2 nitrogen atoms;

or, if X is $C_1$-$C_4$-alkyl, $R^3$ and X together with the interjacent atoms between these radicals form a 5-, 6- or 7-membered ring, which contains besides carbon atoms 1 or 2 nitrogen atoms.

11. The process according to claim 1, wherein the base b2 is 1,8-diazabicyclo[5.4.0]undec-7-ene (DBU), 1,5-diazabicyclo[4.3.0]non-5-ene (DBN), or 1,5,7-triazabicyclo[4.4.0]dec-5-ene (TBD).

12. The process according to claim 1, wherein the base b2 is used in an amount that ranges between 1 and 20 mol %, based on the aromatic chloride of formula II.

13. The process according to claim 1, wherein the process is conducted at a temperature between 50° C. and 150° C.

14. The process according to claim 1, wherein the process is conducted at a pressure between 500 and 1500 kPa.

15. The process according to claim 1, wherein the palladium-based catalyst is prepared from Pd(II) compounds or Pd(0) compounds by complexing with monodentate or bidentate phosphine ligands.

16. The process according to claim 1, wherein the palladium-based catalyst is prepared from Pd(II) compounds or Pd(0) compounds by complexing with monodentate or bidentate phosphine ligands selected from the group consisting of triphenylphosphine, tri(tolyl)phosphine, tri-n-butylphosphine, tricyclohexylphosphine, tri-tert-butylphosphine, S-phos (2-dicyclohexylphosphino-2',6'-dimethoxybiphenyl), cyclohexyldiphenylphosphine, tri-isopropylphosphine, phenyldicycloheylphosphine, butyldiadamantylphosphine, 1,2-Bis(dimethylphosphino)ethane, 2,2'-Bis(diphenylphosphino)-1,1'-binaphthyl (BINAP), 2-Bis(diphenylphosphino)ethane (DPPE), 1,3-Bis(diphenylphosphino)-propane (DPPP), 1,4-Bis(diphenylphosphino)butane (DPPB), 1,1'-Bis(diphenylphosphino)ferrocene (DPPF), 4,5-Bis(diphenylphosphino)-9,9-dimethylxanthene (Xantphos), Bis(2-diphenylphosphino)phenyl]ether (DPEphos), 1,2-Bis(di-tert-butylphosphinomethyl)benzene, 1,2-Bis(di-tert-pentylphosphinomethyl)benzene, 1,2-Bis(di-tert-butylphosphinomethyl)naphthaline, 2,2-dimethyl-1,3-Bis(diphenylphosphino)-propane, 1,3-Bis(diisoproylphosphino)-propane (DiPrPP), 1,3-Bis(tert-butylphosphino)-propane (DtBuPP), 1,3-Bis(n-butylphosphino)-propane (DnBuPP), 1,3-Bis(diisoproylphosphino)-ethan (DCPE), 1,3-Bis(dicyclohexylphosphino)-butane (DCPB), (1R)-1-[Bis(1,1-dimethylethyl)phosphino]-2-[(1R)-1-[Bis(2-methylphenyl)phosphino]ethyl]ferrocene, (2R)-1-[(1R)-1-[Bis(1,1-dimethylethyl)phosphino]ethyl]-2-(dicyclohexylphosphino)ferrocene, (2R)-1-[(1R)-1-(dicyclohexylphosphino)ethyl]-2-(diphenylphosphino)ferrocene, (1R)-1-(dicyclohexylphosphino)-2-[(1R)-1-(dicyclohexylphosphino)ethyl]ferrocene, 2-ethyl-2-butyl-1,3-Bis(diphenylphosphino)-propane, and 1,3-Bis(dicyclohexylphosphino)-propane (DCPP); and wherein the molar ratio of the phosphine ligand to palladium is between 0.5:1 to 5:1.

* * * * *